United States Patent [19]
Hemmings et al.

[11] Patent Number: 5,357,785
[45] Date of Patent: Oct. 25, 1994

[54] METHOD AND DEVICE FOR DETERMINING RHENOLOGICAL PROPERTIES

[75] Inventors: Raymond T. Hemmings, Mississauga; Edward G. Kimber, Burlington, both of Canada

[73] Assignees: Radian Corporation, Austin, Tex.; Inco Limited, Canada

[21] Appl. No.: 72,980

[22] Filed: Jun. 4, 1993

[51] Int. Cl.$^5$ .................................................. G01N 11/14
[52] U.S. Cl. ................................................................ 73/54.32
[58] Field of Search .................. 73/54.31, 54.32, 54.33, 73/54.35, 54.28, 54.29

[56] References Cited

U.S. PATENT DOCUMENTS

| | | | |
|---|---|---|---|
| 2,917,065 | 12/1959 | Monk | 73/54.32 X |
| 3,343,405 | 9/1967 | Gilinson, Jr. et al. | 73/54.34 |
| 3,875,791 | 4/1975 | Fitzgerald et al. | 73/54.31 |
| 4,062,225 | 12/1977 | Murphy, Jr. et al. | 73/54.35 |
| 4,299,119 | 11/1981 | Fitzgerald et al. | 73/54.28 |
| 4,524,611 | 6/1985 | Richon et al. | 73/54.35 |
| 4,535,621 | 8/1985 | Gervais et al. | 73/54.23 |
| 4,879,897 | 11/1989 | Booth et al. | 73/54.31 |

FOREIGN PATENT DOCUMENTS

| | | | |
|---|---|---|---|
| 1065736 | 1/1984 | U.S.S.R. | 73/54.32 |
| 1449868 | 1/1989 | U.S.S.R. | 73/54.31 |

OTHER PUBLICATIONS

Tattersall et al., "The Rheology of Fresh Concrete," 1983, pp. 77, 80, 82–83, 87, 89–91 and 262–265.

*Primary Examiner*—Hezron E. Williams
*Assistant Examiner*—Joseph W. Roskos
*Attorney, Agent, or Firm*—Klauber & Jackson

[57] ABSTRACT

A method and device for the measurement of rheological properties of high density slurry materials and in particular high density mill tailings. A sample of the tailings is placed within a mixing tub, with either a concentric paddle or a planetarily movable paddle used to effect the mixing. A digitally controlled electric motor is used to directly drive the paddle at a constant or predetermined speed or speeds. The tub is laterally pivotable against a load cell for a direct determination of reaction torque with correlation to viscosity and other rheological properties of the mill tailing.

19 Claims, 2 Drawing Sheets

METHOD AND DEVICE FOR DETERMINING RHENOLOGICAL PROPERTIES

FIELD OF THE INVENTION

This invention relates to the determination of rheological properties of high density slurry type materials such as concrete and in particular high density mill tailings.

BACKGROUND OF THE INVENTION

The standard devices in the field of measurement of rheological properties of concrete are described by GH Tattersall and PFG Banfill ("Tattersall"), in chapter 6 of their treatise, *The Rheology of Fresh Concrete* (Pitman Publishing Inc. 1983). The various devices described, all involve the mixing of the concrete in a bowl by either concentric or planetarily movable paddles, driven through an electric motor with an hydraulic transmission. Mixing torque, with correlation to concrete viscosity and other rheological properties of the concrete, is determined by variations in oil pressure in the hydraulic gear box, occasioned by the torque of mixing.

While such devices provide some measurement of the rheological properties of concrete, there are inherent properties of the system which result in substantial measuring errors. Since the mixing torque is measured by monitoring oil pressure in the hydraulic gearbox there is no allowance for energy losses in the drive system between the hydraulic gearbox and the mixing paddle. In addition, there is no provision for oil temperature corrections which cause pressure and measurement deviations.

In addition, while the Tattersall device provides some degree of accuracy with concrete, its indirect torque measurements are not suitable for accurate measurement of the rheological properties of high density mill tailings, which have completely different "aggregate" gradations, and different water to solids ratios by an order of magnitude. The tailings also interact chemically with the binder system, with deviations resulting from different products and their rheological properties, as well as diminution of reactant materials.

SUMMARY OF THE INVENTION

It is an object of the present invention to provide a method and device for the accurate rheological property measurement of both concrete and high density mill tailings.

It is a further object of the present invention to provide such method and device for the rheological property measurement of mill tailings without the inherent inaccuracies of prior art devices.

It is another object of the present invention to provide a device with continuous constant paddle speed and wherein reaction torque causes emission of an electrical signal directly proportional to such torque.

It is a still further object of the present invention to provide a method and device for measurement of the rheological properties of high density mill tailings or other high density slurry materials with minimal mechanical, frictional, or inertia losses.

These and other objects, features and advantages of the present invention will become more evident from the following discussion and drawings in which:

SHORT DESCRIPTION OF THE DRAWINGS

DETAILED DESCRIPTION OF THE INVENTION

Figure 1:
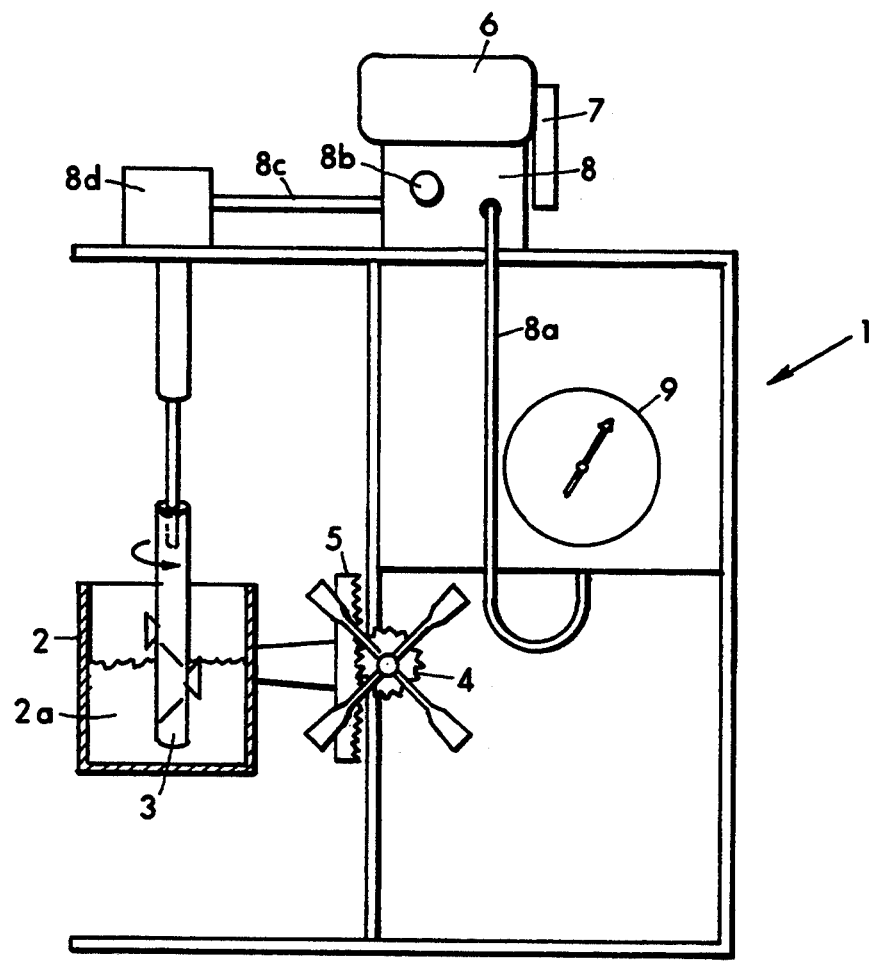
FIG. 1 depicts the prior art Tattersall device as depicted in FIG. 6.5 of *The Rheology of Fresh Concrete;*

Generally the present invention comprises a method and device for the determination of rheological properties of high density slurry type materials such as concrete and in particular high density mill tailings. The device comprises support means for supporting a container having a representative sample of the slurry type material therein for rheological property testing. The device further comprises means for mixing the sample within the container at one or more substantially known rates of speed throughout the mixing. In order to directly measure the mixing torque, the device is provided with means for permitting the container to move during the mixing with a displacement directly related to the torque of the mixing. Monitoring means is included, for monitoring torque-induced displacement of the container for direct determination of the torque of mixing and the rheological properties of the material.

The method of the present invention, for the rheological property determination of a slurry type material, comprises the constant speed or known-speed mixing of high density slurry type materials such as mill tailings, wherein the mixing causes displacement of the mixing container in a manner directly related to the mixing torque. In accordance with the present method:

a) a representative sample of the slurry type material is placed into a container;

b) the sample is mixed, within the container, at one or more substantially known rates of speed, wherein the container moves, during the mixing, with a displacement directly related to the torque of the mixing;

c) displacement of the container is monitored, during the mixing, for direct determination of the torque of mixing and the rheological properties of the slurry sample.

In a preferred embodiment, the device comprises a digitally controlled electric motor mounted directly tea reducing gearbox, with helical gears, to ensure smooth operation. The paddle speed can be set to accelerate at a known rate between two speeds. In any event, paddle speed is always known.

The motor, gearbox and paddle are mounted in a fixed position, relative to the container which is mounted in a vertically movable manner, whereby the paddle can be readily immersed and removed from the material being tested. The mixing paddle itself is preferably either concentric or operates with a planetary motion in a manner similar to that of the Tattersall device. Preferably, the paddle is H-shaped.

However, in contrast to the Tattersall device, as well as other devices in the field, the container or tub containing the sample material is displaced during mixing, with low friction losses, in a plane horizontal to the mixing torque, whereby such displacement is in direct relation to the mixing torque.

In accordance with the present invention, the low friction loss, horizontal plane displacement of the tub is preferably effected by mounting the tub on a movable plate which is movably affixed to a fixed member. Specifically, movable plate is a swivel plate support, which is mounted on a fixed plate. The swivel plate support is pivotally connected to the fixed plate by a fixed pivot connection, which in one embodiment is off-center, relative to the paddle axis. A horizontal roller element bearing supports the swivel plate about the fixed pivot. Two vertically mounted roller element bearings support the outboard end of the swivel plate and are set perpendicular to radial lines through the fixed pivot. The rolling element bearings keep the swivel plate support and fixed plate in stable, spaced, though relatively movable relation. The torque of mixing causes the tub, with swivel plate support, to swivel on the surface of the fixed plate. This motion between the two plates is restrained by a load cell, which joins the two support plates, at a distance from the fixed pivot point whereby torque reacting on the swivel plate causes a proportional straining of the load cell.

The load cell emits an electrical signal directly proportional to the torque experienced by the swivel plate. The signal is then recorded on an x-y chart recorder for later correlation with rheological properties of materials which provide the measured torque at the known speed or speeds of mixing.

Because the reaction torque is monitored directly on the tub, mechanical losses in the drive train to the paddle, which may be quite large, are of no consequence in the reaction torque determination. The torque measured by the load cell is equal to the mixing torque, less the friction torque of the swivel plate support and the inertia torque of the tub involved in the movement of the swivel plate about the fixed pivot. However, in accordance with the present invention, such inertia and friction losses are minimized to negligibility.

The load cell is, in effect, a very stiff spring element with a very small deflection and, as a result, actual movement of the tub is very small and it is essentially stationary and concentric with the paddle axis. Thus, for example, a load cell useful in the operation of the present invention provides a 0.004" (0.01 cm) deflection for a load of 100 lbs (45.4 kg). The rheometer of the present invention is typically designed to operate with loads up to 25 lbs (11.4 kg) which provides a representative sample of the slurry to be measured. Since the mixing tub is positioned between the load cell and the fixed pivot, the full range horizontal travel of the tub is less than 0.001" (0.003 cm). When measuring torque at a specific speed, the effects of such displacements are negligible and can be ignored without significant effect on accuracy. Frictional effects are minimized by the use of lightly loaded rolling element bearings to support the mixing tub and such frictional effects can also be ignored. As a result, the torque detected by the load cell is essentially only the torque of mixing.

Calibration of the torque measuring device is easily effected by removing the load cell and measuring its load/output signal with dead weights. Since the load cell is always at a known distance from the pivot, the torque/signal is readily accurately established. Accuracy of speed setting can be checked by timing a known number of revolutions of the paddle.

To avoid any errors which may result from vibration and unwanted component movements it is highly preferred that the device have a high rigidity which resists such movement. In addition, for both smooth operation and longevity under high stress conditions, it is preferred that the motor be a high torque/high power one, though it may be of any controlled type such as electric, hydraulic, etc.

DETAILED DESCRIPTION OF THE DRAWINGS AND THE PREFERRED EMBODIMENT

With specific reference to the drawings, in FIG. 1, the prior art Tattersall device 1, described as the MkII apparatus, is shown with electric drive motor 6, belt drive 7, speed control 8b and reduction gear 8d. Drive shaft 8c which provides the requisite mixing torque to impeller 3 is driven through hydraulic transmission 8. Interrupted helix impeller 3 is immersed into bowl 2 containing the material 2a (specifically fresh concrete) for testing of the rheological properties thereof. Rack and pinion gears 4 and 5 serve to raise and lower bowl 2 for mixing engagement and disengagement with impeller 3. Rotation of impeller 3 for mixing of the material 2a, with material resistance, causes fluctuations in the hydraulic pressure in the transmission. Transmission oil carrying hose 8a connects transmission 8 to pressure gauge 9 for measurement of such fluctuations. The indirect pressure measurements are then correlated to mixing torques at specific speeds and then to rheological properties such as materials viscosity.

Figure 2:
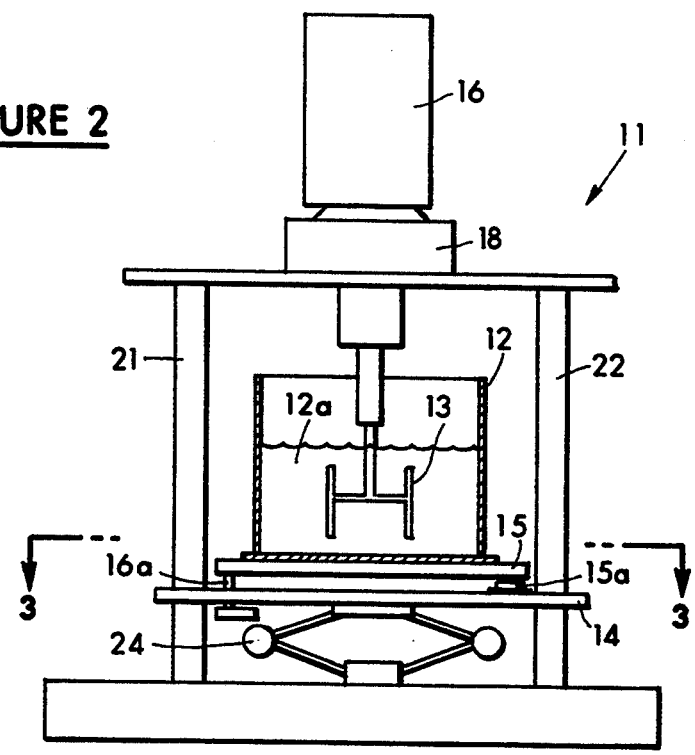
FIG. 2 is a partially sectioned elevational schematic view of the device of the present invention.

As shown in FIG. 2, the rheological measurement device 11 of the present invention comprises a digitally controlled electric motor 16 directly in line with gear box 18 without intervening hydraulic transmission. H-configured paddle 13 is thus directly driven by motor 16 without an intervening hydraulic transmission. Laterally fixed support plate 14 is raised and lowered by scissor jack 24 along support columns 21-23. Swivel plate 15, which directly supports mixing tub 12 containing the material under test 12a, is connected to fixed support plate 14 via pivot 15a containing a horizontally disposed roller bearing member (not shown).

Figure 3:
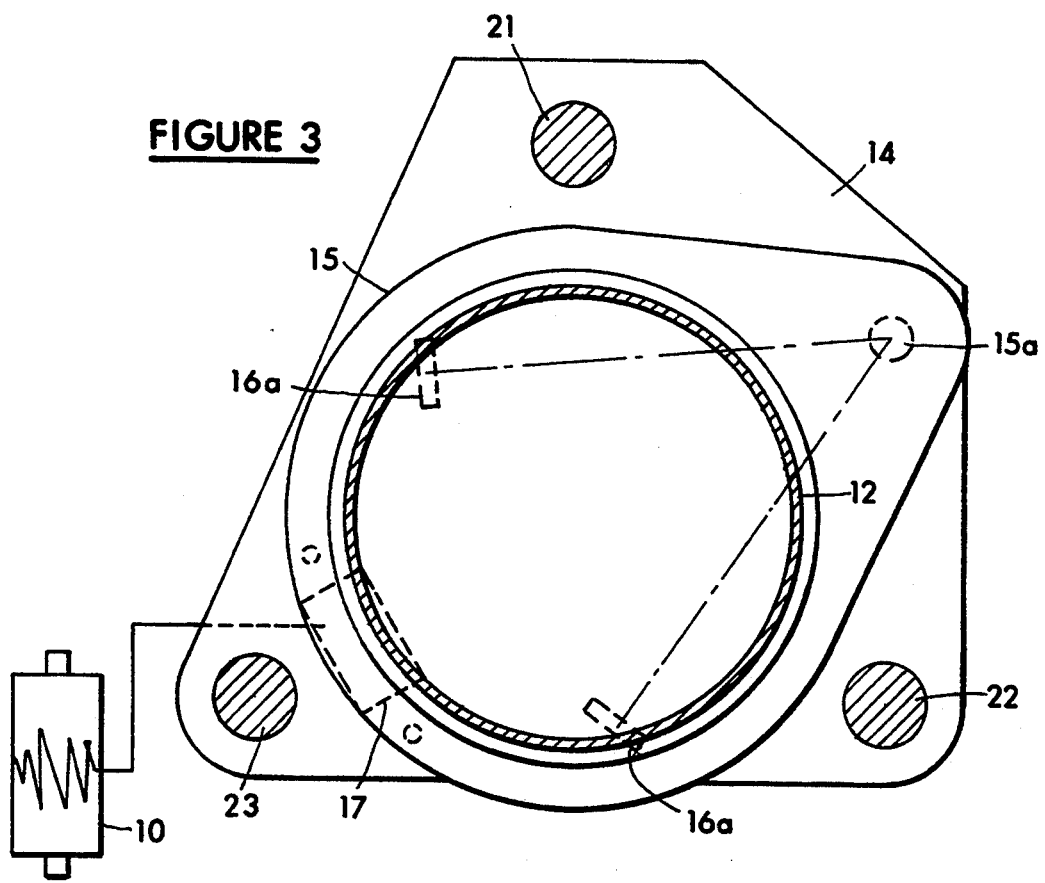
FIG. 3 is a top view of the stationary and swivel plate of the FIG. 2 taken along line 3—3.

As is more clearly seen in FIG. 3, roller bearings 16a and 16b are vertically disposed between stationary plate 14 and swivel plate 15 and are set at right angles relative to radial lines passing through fixed pivot 15a. This corresponds to the swivel movement of swivel plate 15 and tub 12 to effectively negate frictional losses. Load cell 17, connected to both swivel plate 15 and stationary plate 14 minimizes the swivel movement while directly measuring mixing torque of test material 12a. The load cell displacements are recorded on x-y chart recorder 10 for relation to the known impeller speeds and correlation to known rheological properties.

It is understood that the above description and drawings are illustrative of the present invention and that changes in testing device structure and operation are possible without departing from the scope of the present invention as defined in the following claims.

What is claimed is:

1. A device for the rheological property determination of a slurry type material, the device comprising support means for supporting a container having a sample of the slurry type material therein, said device further comprising means for mixing the sample within said container at one or more substantially known rates of speed throughout the mixing, means for permitting the container to move during the mixing with a displacement substantially directly related to the torque of the mixing, and load cell means mounted on said device and being responsive to the induced displacement of the container by generating an electrical signal proportional to the torque, for direct determination of the torque of mixing and thereby of the rheological properties of the material.

2. The device of claim 1, wherein the means for mixing the sample comprises a digitally controlled electric motor, a mixing paddle, and a direct drive between the motor and paddle.

3. The device of claim 2, wherein the paddle comprises a planetary movable paddle having an H-configuration.

4. The device of claim 2, wherein the support means is movable relative to the paddle whereby the container, having the sample therein, is movable into and out of operative engagement with the paddle for the mixing of the sample.

5. The device of claim 1, wherein the support means embodies means which permits the container to move in a lateral direction relative to the paddle, with said lateral movement comprising a motion related to the torque of mixing.

6. The device of claim 5, wherein the support means comprises a plate member, movable in the lateral direction, with the container being directly supported by the plate member, and wherein the plate member is supported on a fixed member.

7. The device of claim 6, wherein the plate member is supported on the fixed member by roller bearings, which bearings permit the lateral movement of the plate member, and supported container, with minimal frictional losses.

8. The device of claim 7, wherein said load cell means is affixed to the plate member and the fixed member, wherein displacement of the container during mixing causes displacement of the plate member and deflection of the load cell, said deflection generating said electrical signal.

9. The device of claim 8, wherein the load cell provides a maximum deflection of 0.004" (0.01 cm) for a load of 100 pounds (45.4 kg).

10. The device of claim 8, wherein the plate member comprises a swivel plate support, and the fixed member comprises a fixed plate, the swivel plate support being pivotally connected to the fixed plate by a fixed pivot connection, which is off-center, relative to the paddle, with a horizontal roller element bearing supporting the swivel plate about the fixed pivot, with vertically mounted roller element bearings supporting an end of the swivel plate distant from the pivot connection, the vertically mounted roller element bearings being positioned perpendicular to radial lines through the fixed pivot connection, whereby the rolling element bearings keep the swivel plate support and fixed plate in stable, spaced, though relatively movable relation, when the torque of mixing causes the container, with swivel plate support, to swivel on the surface of the fixed plate.

11. A method for the rheological property determination of a slurry type material, comprising the steps of:
   a) placing a sample of said slurry type material into a container mounted on a movable plate which is movably attached to a fixed member;
   b) mixing the sample, within the container, at one or more substantially known rates of speed, wherein the container and movable plate moves, during the mixing relative to the fixed member, with a displacement directly related to the torque of the mixing;
   c) monitoring the displacement of the container, during said mixing by generating an electrical signal at a load cell which is connected between the movable plate and fixed member, for direct determination of the torque of mixing and thereby of the rheological properties of the slurry sample.

12. The method of claim 11, wherein said material comprises mill tailings.

13. The method of claim 11, wherein the means for mixing the sample comprises a digitally controlled electric motor, a mixing paddle, and a rigid drive between the motor and paddle.

14. The method of claim 13, wherein the paddle comprises a planetary movable paddle having an H-configuration.

15. The method of claim 11, wherein the support means is movable relative to the paddle whereby the container, having the sample therein, is movable into and out of operative engagement with the paddle for the mixing of the sample.

16. The method of claim 11, wherein said plate, is movable in the lateral direction, with the container being directly supported by the plate, and wherein the plate is supported on said fixed member.

17. The method of claim 16, wherein said plate is supported on said fixed member by roller bearings, which bearings permit the lateral movement of the plate, and supported container, with minimal frictional losses.

18. The method of claim 17, wherein said load cell is affixed to the plate and the fixed member, wherein displacement of the container during mixing causes displacement of the plate and deflection of the load cell, said deflection being monitored as said electrical signal.

19. The method of claim 18, wherein the load cell provides a maximum deflection of 0.004" (0.01 cm) for a load of 100 pounds (45.4 kg).

* * * * *